United States Patent
Hartmann et al.

(10) Patent No.: US 11,759,652 B2
(45) Date of Patent: Sep. 19, 2023

(54) PORTABLE APPARATUS FOR DECONTAMINATION OF A BREAST

(71) Applicant: Carag AG, Baar (CH)

(72) Inventors: Peter Hartmann, Goosebery Hill (AU); Michael Larsson, Zug (CH); Kuno Limacher, Steinhausen (CH); Jerome Bernhard, Zurich (CH); Lukas Christen, Lucerne (CH); Simona Wiedmer, Zug (CH); Daniel Napoletano, Eglisau (CH)

(73) Assignee: Carag AG, Baar (CH)

( * ) Notice: Subject to any disclaimer, the term of this patent is extended or adjusted under 35 U.S.C. 154(b) by 245 days.

(21) Appl. No.: 17/245,274

(22) Filed: Apr. 30, 2021

(65) Prior Publication Data

US 2021/0244966 A1 Aug. 12, 2021

Related U.S. Application Data

(63) Continuation of application No. 16/324,245, filed as application No. PCT/EP2017/070250 on Aug. 9, 2017, now Pat. No. 11,007,379.

(30) Foreign Application Priority Data

Aug. 9, 2016 (EP) ..................................... 16183310

(51) Int. Cl.
*A61N 5/06* (2006.01)
*A61L 2/00* (2006.01)
(Continued)

(52) U.S. Cl.
CPC .......... *A61N 5/0624* (2013.01); *A41C 3/0064* (2013.01); *A41C 3/04* (2013.01);
(Continued)

(58) Field of Classification Search
CPC .... A61L 2/0011; A61L 2/0047; A61L 2/0094; A61L 2/025; A61L 2/10; A61N 5/0624
See application file for complete search history.

(56) References Cited

U.S. PATENT DOCUMENTS

| 8,753,171 B2 | 6/2014 | Thompson |
| 2003/0073930 A1 | 4/2003 | Morrissey et al. |

(Continued)

FOREIGN PATENT DOCUMENTS

| CN | 201046247 Y | 4/2008 |
| CN | 202154891 U | 3/2012 |

(Continued)

OTHER PUBLICATIONS

International Search Report, PCT/EP2017/070250, dated Oct. 16, 2017.

(Continued)

*Primary Examiner* — Sean E Conley
(74) *Attorney, Agent, or Firm* — Fishman Stewart PLLC

(57) ABSTRACT

A portable device for the decontamination of a breast. The aim of the device is to reduce the risk of mastitis, even when the patient has a medicament incompatibility. For this purpose, the invention includes a decontamination unit which decontaminates the breast at least by means of a physical method.

17 Claims, 15 Drawing Sheets

(51) Int. Cl.
  *A61L 2/025* (2006.01)
  *A61N 1/44* (2006.01)
  *A41C 3/04* (2006.01)
  *A61M 1/06* (2006.01)
  *A61L 2/14* (2006.01)
  *A61L 2/10* (2006.01)
  *A41C 3/00* (2006.01)
  *A61N 7/00* (2006.01)

(52) U.S. Cl.
  CPC .......... *A61L 2/0011* (2013.01); *A61L 2/0047* (2013.01); *A61L 2/0094* (2013.01); *A61L 2/025* (2013.01); *A61L 2/10* (2013.01); *A61L 2/14* (2013.01); *A61M 1/062* (2014.02); *A61L 2202/14* (2013.01); *A61L 2202/15* (2013.01); *A61L 2202/16* (2013.01); *A61M 2202/0216* (2013.01); *A61M 2205/053* (2013.01); *A61M 2205/054* (2013.01); *A61M 2205/058* (2013.01); *A61N 1/44* (2013.01); *A61N 2005/0644* (2013.01); *A61N 2005/0649* (2013.01); *A61N 2005/0651* (2013.01); *A61N 2005/0661* (2013.01); *A61N 2007/0004* (2013.01); *A61N 2007/0034* (2013.01)

(56) References Cited

U.S. PATENT DOCUMENTS

| | | |
|---|---|---|
| 2008/0106896 A1 | 5/2008 | Liu et al. |
| 2012/0209124 A1 | 8/2012 | Shieh et al. |
| 2016/0346565 A1 | 12/2016 | Rhodes et al. |

FOREIGN PATENT DOCUMENTS

| | | |
|---|---|---|
| CN | 203915153 U | 11/2014 |
| CN | 204180955 U | 3/2015 |
| CN | 204446739 U | 7/2015 |
| JP | 05096018 | 4/1993 |
| RU | 2549325 C1 | 4/2015 |
| WO | WO 2006/099413 A2 * | 11/2000 |
| WO | 2006037599 A1 | 4/2006 |
| WO | 2011144344 A2 | 11/2011 |
| WO | 2015088948 A1 | 6/2015 |
| WO | 2016196395 A1 | 12/2016 |

OTHER PUBLICATIONS

Definition of "snap". Webster Dictionary (Year: 2020).
U.S. Appl. No. 16/324,245, filed Feb. 8, 2019, Peter Hartmann et al.

* cited by examiner

PORTABLE APPARATUS FOR DECONTAMINATION OF A BREAST

CROSS-REFERENCE TO RELATED APPLICATIONS

This application is a continuation of U.S. patent application Ser. No. 16/324,245, filed Feb. 8, 2019, which claims priority to International Application PCT/EP2017/070250 filed on Aug. 9, 2017 and to European Application EP 16183310.8 filed on Aug. 9, 2016, the contents of each are hereby incorporated by reference in their entirety.

TECHNICAL FIELD

The present invention relates to a portable apparatus for decontamination of a breast.

BACKGROUND

A generic apparatus having the features according to the preamble of claim 1 is known, for example, from US 2003/0073930 A1. The apparatus described in this document comprise a bell that is slipped over a human female breast. Disposed within the bell is a pressure element, on the surface of which absorbent material is attached. The pressure applied by the pressure element forces the absorbent material against the nipple to either absorb moisture therefrom or to apply a medical reagent such as a fungicidal or antibacterial reagent. This heals or reduces, for example, an inflammation of the breast.

There is an increased risk of mastitis for the lactating breast of a mother. The reason for this being that, after milk has been removed, for example by expressing it or through the baby, the milk ducts are still open, which can lead to an invasion of pathogens.

Although the system known from US 2003/0073930 A1 can reduce the risk of mastitis, it can happen, however, that the respective patient does not tolerate the medication with which the absorbent material is impregnated.

In the light of this problem, the present invention proposes a portable apparatus for decontamination of a breast having the features of claim 1.

The portable decontamination apparatus is characterized in particular by the fact that the decontamination unit decontaminates the breast by way of a physical method.

By employing such a physical method, no liquid or pasty substance needs to be used for decontamination. In contrast to biological or chemical decontamination methods, at least physical decontamination is presently performed. A physical variable is therefore used as a way of contamination. This variable is generated, for example, by way of electrical energy, and the breast is exposed to the variable generated by way of electrical energy.

It is advantageous with such physical decontamination that it does not act only against individual species of microorganisms, but in a "broad spectrum" against a variety of microorganisms. The term "microorganism" is used as follows in this context. Microorganisms can be microscopic creatures (organisms) that are not recognizable as individual creatures with the naked eye. They are also referred to as microbes. They do not form a homogenous group in the system of living creatures. Microorganisms include bacteria (e.g., lactic acid bacteria), fungi (e.g., baker's yeast), microscopic algae (e.g., chlorella), and protozoa (e.g., paramecia and the malaria parasite plasmodium). In the present case, viruses are also included as microorganisms. Although viruses are predominantly not considered as being living beings, therefore also not as being microorganisms, occasionally, however, they are included in microorganisms, and then virology is accordingly considered to be a branch of microbiology.

In addition, such physical decontamination has the advantage that no resistances arise, as is the case when e.g. antibiotics (chemical reagents) are used for decontamination.

Also, treatment is possible during the time of breastfeeding children because the nipple is available without residue for the children for food intake.

According to one advantageous development of the invention, this decontamination unit can contain at least one of the following elements: a light source, in particular a UV light source, an ultrasound source, an ozonization source, a plasma source, in particular a cold plasma source. These sources all generate energetic/highly energetic radiation and/or energetic/highly energetic particles and/or energetic/highly energetic molecules and/or energetic/highly energetic waves which interact with respective pathogens such as bacteria and viruses for decontamination in order to render them harmless. To generate this radiation or these particles e.g. an energy source, in particular an electrical energy source is used.

An LED, in particular a UV LED, can be employed as the light source. For example, a piezoceramic element can be employed as the ultrasound source. Both of the aforementioned elements can nowadays be produced to be very small and can be mounted in the immediate vicinity of the location on the breast to be decontaminated.

In particular, a UV-C light source is used as the light source or excitation radiation source. Such UVC light is also referred to as remote UV light and is distinguished from near UV light (UV-A or black light) and medium UV light (UV-B) by way of the wavelength.

In particular, UVC light has a wavelength of 280 to 100 nm and photon energy of 4.43 eV to 12.4 eV. UV-C light can be further subclassified in UVC-FUV having a wavelength range of 280 to 200 nm and photon energy of 4.43 eV to 6.20 eV and UVC-VUV having a wavelength range of 200 nm to 100 nm and photon energy of 6.20 eV to 12.4 eV. Below 200 nm (UVC-VUV), the ultraviolet radiation is so shortwave and energetic that it is absorbed by molecular oxygen. The molecular oxygen is then split into two free oxygen radicals, each of which reacts with another oxygen molecule to form ozone.

When UVC-VUV radiation is presently use, decontamination is also created by the resulting ozone, in addition to the decontamination by the radiation itself.

The UV-C light does not penetrate very deeply into the skin due to the relatively short wavelength and thence high scattering. For example, while the amino acid tryptophan is damaged or degenerated at 280 nm, the nucleic acids are most damaged at 265 nm.

Accordingly, the following wavelength ranges of radiation are preferably used in the present invention.

According to one advantageous development of the invention, the apparatus can have a bell-like structure which can be slipped over the breast and surrounds it, at least in part. This bell-like structure can therefore be slipped over the breast. The bell-like structure can in this case already be pre-formed such that it can be donned onto the breast. The respective decontamination unit can then be provided within this bell-like structure. The bell-like structure ensures that the region of the breast to be decontaminated is sealed off from the exterior ambient atmosphere, and that the region of the breast surface within the bell is efficiently decontaminated. This bell-like structure can be a kind of cap which is slipped over the breast.

The bell-like structure can be formed substantially by a front-side widened portion facing the breast and formed like a funnel. A cylindrical tube extends from the side of the widened portion facing away from the breast e.g., toward the back. This tube is also referred to as a conical taper and preferably has a diameter that is less than the opening of the widened portion that is slipped over the breast. The bell-like structure and the adjoining conical taper can be formed integrally and from unitary material. These elements can also be configured as several parts.

According to one advantageous development of the invention, the bell-like structure can be formed such that it takes shape instantaneously only when donned onto to the breast and preferably returns to its initial state when removed from the breast. In an initial state not donned onto the breast, the bell-like structure can also be configured to be, e.g., a flat component which has no bell-like structure. Only when donned onto the breast does the bell-like structure take shape instantaneously. When removed from the breast, the element again returns to its initial state.

According to one advantageous development of the invention, the bell-like structure can be adapted in such a way that the breast abuts thereagainst in true contour and that a recess is formed on its inner side in the region of the nipple. It is possible with this abutment in true contour to place the decontamination unit as a single element at a well-defined location and in close proximity to the region of the breast to be treated without regions on the breast surface, which are not to be decontaminated, being acted upon by energetic radiation or particles.

The decontamination unit can comprise e.g., a housing in which one or more excitation radiation sources are provided. The housing can be a separate element which is detachably mountable on the apparatus. This has the advantage that the decontamination unit, in which, for example, electronics are provided, is not exposed to water when the bell-like structure or other parts of the apparatus are rinsed with water. In addition, this configuration has the advantage that the decontamination unit can also be attached to differently configured bell-like structures.

The decontamination unit can contain, e.g., one or more excitation radiation sources. This excitation radiation source is a source with which physical decontamination is effected. Such an excitation radiation source can be, for example, a UV radiation source, in particular a UV-C radiation source, a plasma radiation source, an ultrasound radiation source or an ozonization source.

The decontamination unit with its housing can be configured such that the housing can be secured by being snapped onto the apparatus for decontamination of the breast, in particular at a section of a widened region which can be slipped over the breast and/or at a section of a cylindrical tube projecting from the side of the widened region facing away from the breast.

Particularly simple assembly and disassembly of the decontamination unit is then possible.

In the apparatus, electronics for operating the decontamination unit can be connected only on the housing. The apparatus for decontamination of the breast may have no other source of excitation radiation except on the housing.

It has turned out to be advantageous having an excitation radiation source be provided neither on the widened portion nor on the cylindrical tube itself. It is advantageous to provide the excitation radiation source or the excitation radiation sources only in the housing of the decontamination unit which is configured as a separate element. This ensures that e.g. no electronics, at least no electronics for operating the decontamination unit, are provided on the apparatus (with the exception of the separate housing of the decontamination unit).

The housing of the decontamination unit can surround the widened region and/or the cylindrical tube radially on the outside. This ensures simple mounting. It can be favorable, in particular, to form the housing of the decontamination unit as a kind of collar which is placed around the cylindrical tube and/or the widened region. In particular, this collar can have a C-shaped cross-section in order to be fastened to the cylindrical tube by way of a snap connection and therefore preferably in a positive-fit manner.

It has turned out to be favorable to have the widened region and/or the cylindrical tube be transparent to excitation radiation from the decontamination unit, in particular UV-C transparent, at least in a section where an exciter radiation source is placed in a decontamination unit mounted thereon.

It is also conceivable that the housing of the decontamination unit is inserted into the widened region and/or the cylindrical tube and can be operated by way of an induction element placed on the outside of the widened region and/or cylindrical tube.

The induction element can be integrally provided on the bell-like structure, but also as a separate element. For assembly and operation of the decontamination unit, therefore, the collar with the excitation radiation source is inserted into the widened region and/or the cylindrical tube in a first step, and the induction element is then mounted from the outside at the widened region and/or the cylindrical tube. This induction element can also be configured in the manner of a collar. It can also be attached in a positive-fit and/or a force-fit manner, for example, with magnets.

The decontamination unit can also have an exciter radiation source which is provided integrally and captively on a base member. This base member can be coupled to the bell-like structure. Lines for operating the exciter radiation source can be passed through the base member, and contact elements, via which a voltage supply can be connected, can be provided externally on the base member.

Devices with which a battery pack can be repeatedly attached and detached and connected to the contact elements can be provided in the region of the contact elements.

The decontamination unit can comprise an exciter radiation source which is integrally arranged on the base member, where the base member is detachably mountable on the rear side of the bell-like structure.

According to a further advantageous development of the invention, the decontamination unit can abut against the breast after the apparatus has been mounted. The decontamination unit can then preferably have a surface which rests directly on the surface to be treated. Where the bell-like structure in the region of the nipple forms a recess on the inner side, the inner surface, in particular the entire inner surface, of this recess can be formed, for example, by the decontamination unit. Alternatively, a plurality of individual decontamination units can also be provided in this recess, each of which being formed abutting against the nipple.

According to one advantageous development of the invention, at least two decontamination units can be provided at different locations. One or more decontamination unit(s) can then be attached in the recess and/or one or more decontamination unit(s) in the bell-like structure. They are arranged, for example, such that the areola can be decontaminated. One or more decontamination units can be arranged such that they or a group thereof selectively decontaminate the different regions of the breast, namely the nipple, the areola or other breast surface. These decontamination units can have mutually different intensities or degrees of decontamination intensity which are adapted to the different regions. Different regions of the breast can then be selectively decontaminated.

According to one advantageous development of the invention, the decontamination unit or the decontamination units, respectively, can be positioned such that they physically decontaminate the nipple and/or the areola when the apparatus is mounted on the breast. In addition, it can additionally decontaminate the areola when the apparatus is mounted on the breast. As already described, the different decontamination units can in this case have a different decontamination intensity, to the extent that they decontaminate, for example, the nipple or the areola. Such different decontamination intensity can be set via the wavelength of the light radiation, when a light source is used, the energy of an ultrasound source or the amount of ozone or plasma generated.

According to one advantageous development of the invention, the portable apparatus can be a brassiere or an insertion pad, in particular an insertion cushion, or an electrically operated or manually operated breast pump. A portable apparatus is an apparatus that can be carried so easily that it can be used by a single person without great effort and under different circumstances and in different locations. It can be configured to be very compact. The entire apparatus preferably does not exceed the weight of two kilograms, preferably one kilogram. In the case of a brassiere, all possible known types of brassieres can be considered. Breast pumps are used, for example, to express milk from the female breast.

According to one advantageous development of the invention, the decontamination unit can be connected to an autonomous power supply which is integrated into the apparatus. When the apparatus is therefore a brassiere, a manually operated or an electrically operated breast pump, the power supply can be integrated into the respective apparatus. Such a power supply can be a rechargeable battery or a rechargeable accumulator. However, such a power supply can also be a transformer that converts grid voltage to a lower power supply voltage. Preferably, the power supply is combined with the power generation, i.e., it is a rechargeable battery or a rechargeable accumulator.

According to one preferred embodiment of the invention, the decontamination unit can be provided in a pad or a cushion which can be inserted as a separate element into a brassiere, or the decontamination unit can be fixedly mounted on the apparatus. A cushion is understood to be a spongy deformable soft pad. When a pad is used into which the decontamination unit is integrated, the former can be inserted, for example, into pockets provided in the brassiere. However, the pad or the cushion can also be clamped between the breast and the brassiere without it being inserted e.g., into such a pocket. The pad itself accordingly comprises the physical decontamination unit. The pad can form a separate autonomous unit if the power supply and the power generation are integrated therein. In the case of using the apparatus in a breast pump, the decontamination unit can preferably be firmly attached thereto. It is then ensured that the decontamination unit is aligned relative to the breast in a predetermined arrangement, for example, when the decontamination unit is mounted on the rear side within the bell-like structure which forms a suction nozzle for the breast.

Where the decontamination unit in the present invention is provided as a pad or cushion, respectively, then this pad or cushion can also have a tube barb, via which a pump can be connected to express milk from the breast.

Instead of the pad-like or cushion-like structure, the bell-like structure can also be made of a dimensionally stable, e.g., hard material which is in particular configured such that it does not or only slightly collapse upon application of a vacuum. In order for a vacuum to be applicable, it is favorable to have the bell-like structure be vacuum-tight and also be donned in a sealing manner against the breast. The bell-like structure can be formed by a kind of rigid breast shield.

According to one preferred embodiment of the invention, at least one decontamination unit can be respectively arranged on a side of the apparatus facing the breast and on a side facing away from the breast.

According to one advantageous development of the invention, the apparatus can comprise a control device which switches the decontamination unit on and off and/or regulates the intensity. A control device with which the decontamination unit or the decontamination units are controlled can for instance be integrated into the apparatus. Such a control device can be a simple on/off switch which is provided between the voltage supply of the decontamination unit, or be a microcomputer which controls the decontamination unit or the decontamination units in dependence of the requirement after the apparatus has been donned onto the breast. For example, it can be determined using a timer when the pump was applied, and be determined therefrom when the decontamination unit is to be switched on. When several decontamination units are provided, this control device can, for example, selectively control them and/or vary the intensity of the decontamination performance depending on the region in which the decontamination unit is provided on the apparatus.

According to one independent aspect according to claim 12, the invention also relates to the operation of a portable apparatus for decontamination of a breast, as described above. The method is characterized in that the decontamination unit is switched on to kill microorganisms in order to prevent them from entering the mammary ducts. Advantageously, the operation of the apparatus is performed after this apparatus has been mounted on the breast of a female human.

BRIEF DESCRIPTION OF THE DRAWINGS

Further advantageous embodiments of the invention will become apparent from the embodiments explained below in conjunction with the drawings, in which:

FIG. 2b shows the circled region in FIG. 2 c enlarged;

FIG. 7d shows the circled region in FIG. 7c enlarged, FIG. 8d shows the circled region in FIG. 8c enlarged, FIG. 11b shows the circled region in FIG. 11a enlarged.

DETAILED DESCRIPTION

Figure 1:
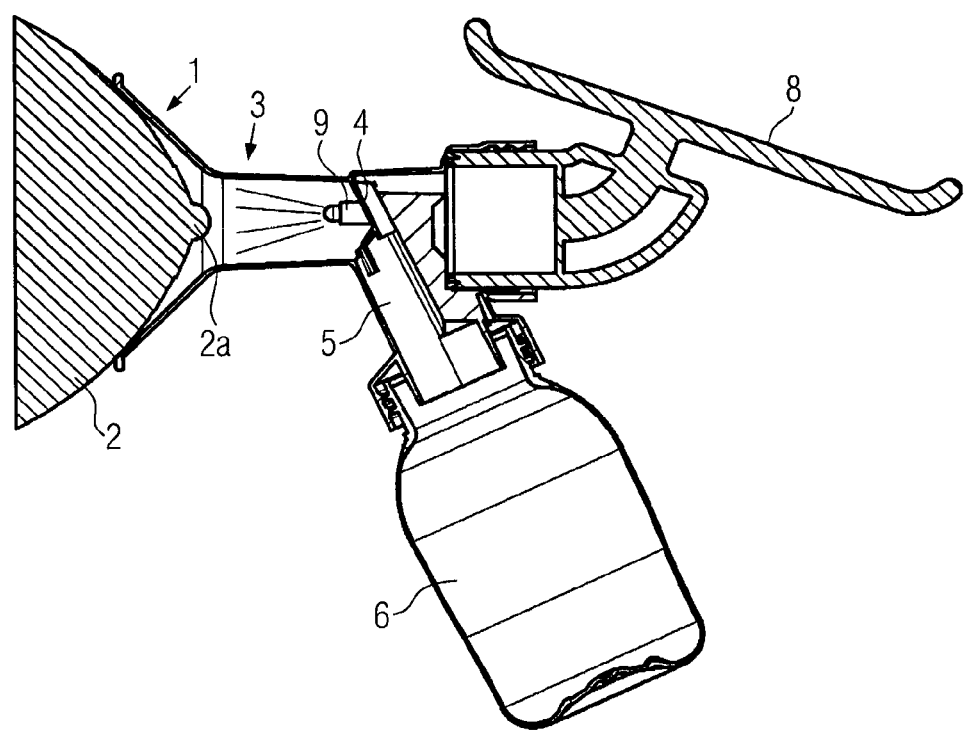
FIG. 1 shows a first embodiment of a manually operated breast pump with a decontamination unit.

The manually operated breast pump shown in FIG. 1 is an example of a portable apparatus for decontamination of a breast 2. This manually operated breast pump comprises a bell-like structure 1 that sealingly surrounds a region of breast 2 such that milk can be expressed from the mammary duct of breast 2. Nipple 2a is positioned in a region of bell-like structure 1 where the latter has a conical tubular taper 3. During the expression process, nipple 2a is therefore advantageously provided in a region of tubular taper 3. On its side 4 disposed opposite to nipple 2a, conical tubular taper 3 comprises a conduit 5 which leads to a collection container 6. Bell-like structure 1 is integrally connected to conduit 5 and a screw cap 7 and thus forms an attachment unit which can be screwed onto collecting container 6. In addition, a lever 8, with which a vacuum can be generated in bell-like structure 1 and in collection container 6, is provided on this attachment unit.

Provided on a wall of conical tubular taper 3 on a side 4 disposed opposite to nipple 2a is a decontamination unit 9. In the present case, this is a UV light-emitting diode (UV LED), the UV light of which radiates onto nipple 2a and at least in part onto areola 10 formed around the nipple.

The UV light-emitting diode is supplied with energy by way of a rechargeable battery, not shown in FIG. 1, which can be inserted into the attachment unit and has a standard dimension. A control device (not shown), with which the UV light-emitting diode can be switched on and off and/or regulated, is also deposed in the attachment unit. As an alternative to the power supply by way of a rechargeable battery, power supply by way of a battery (not rechargeable) is conceivable. Alternatively, a capacitor can also be charged by operating lever 8 which provides the power supply for the UV light emitting diode. Furthermore, provided in the attachment unit can also be a control device which controls the operation of the light-emitting diode such that the latter is switched on when milk is expressed or only shortly after the milk expression has ended. Also, bell-like structure 1 can comprise a contact sensor so that the light-emitting diode only operates when bell-like structure 1 abuts against the breast. This embodiment provides increased safety, especially when a UV-based decontamination apparatus is used, since it prevents operation from taking place when a person can look inside the decontamination unit.

Figure 2A:
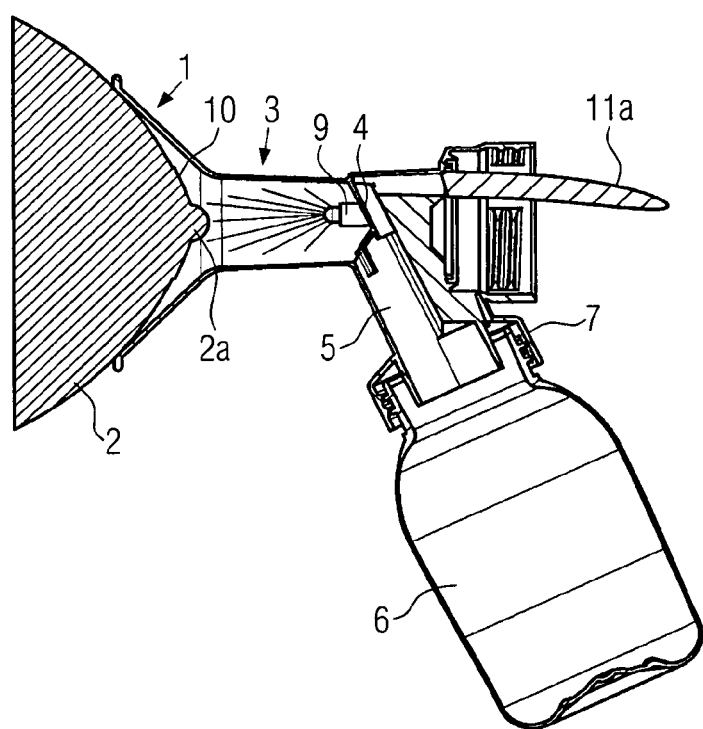
FIGS. 2a, 2b, 2c show a second embodiment of an electrically operated breast pump, where
Figures 2B, 2C:
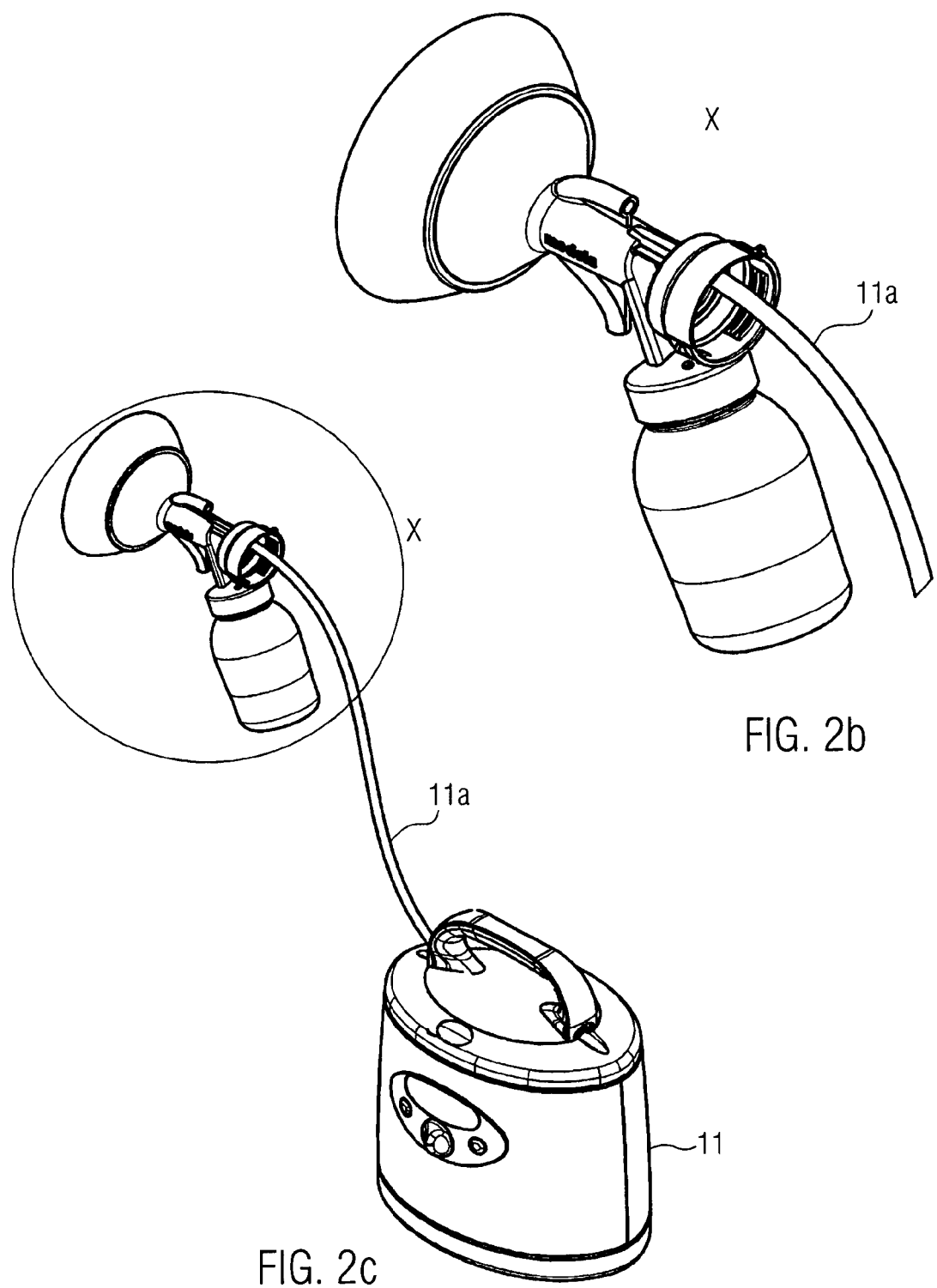

An alternative example of a breast pump is shown in FIGS. 2a, 2b and 2c. The pump itself has the same configuration as the pump in FIG. 1. For this reason, the individual elements shall not be described again. Same elements are denoted with the same reference numerals.

In contrast to the pump of FIG. 1, the embodiment in FIGS. 2a, 2b and 2c is no manually operated pump, but an electrically operated pump.

As can be seen in FIGS. 2a and 2b, a vacuum generating station 11 is provided and is provided separately from the attachment unit and collection container 6. The attachment unit with collection container 6 is connected via vacuum tube 11a to vacuum generating station 11. A cross-sectional view of the attachment unit and collection container 6 can be seen in FIG. 2a. As can be seen, the interior of bell-like structure 1 has the same configuration as in the embodiment of FIG. 1.

In the manually operated pump of FIG. 1, an independent separate power source should be provided in the apparatus. In the electrically operated pump of FIGS. 2a, 2b and 2c, separate power generation can be provided in addition to the power supply for vacuum generating station 11, and/or decontamination unit 9 is supplied with power via vacuum generating station 11.

Figure 3A:
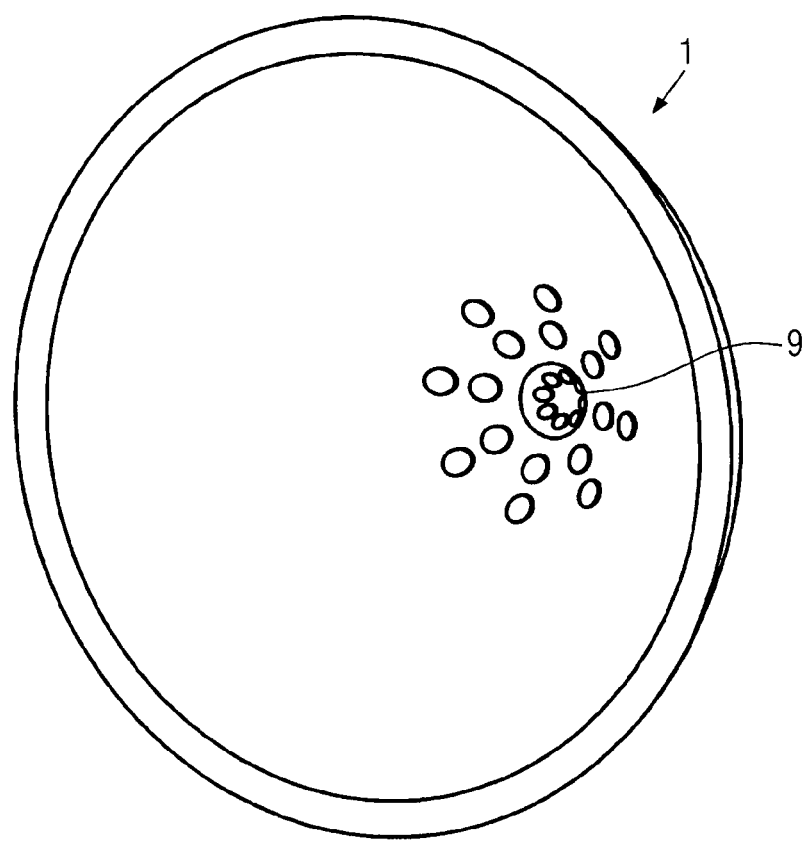
FIG. 3a shows a third embodiment, where the attachment for a breast is configured as a bell-like attachment.

FIG. 3a shows an alternative embodiment of a bell-like structure 1. Bell-like structure 1 in this case is already pre-shaped such that it can be donned onto the breast. In an initial state not donned onto the breast, the bell-like structure can alternatively also be configured to be a flat structure which has no bell-like structure. Only when donned onto breast 2 does bell-like structure 2 shape instantaneously. When removed from breast 2, the element returns to its initial state. As can be seen in the cross-sectional view in FIGS. 3b and 3c, this bell-like structure 1 is configured such that it abuts against breast 2 in a contour-shaping manner. For this purpose, bell-like structure 1 comprises a recess 12 in the region of nipple 2a. Attached in a circular arrangement within recess 12 are individual decontamination units 9. Further decontamination units 9 are provided in bell-like structure 1 outside recess 12 at a small distance from the areola in the region where bell-like structure 1 abuts against the areola. All decontamination units 9 can be controlled by a common control device, not shown. This control device as well as a power supply for the decontamination units can be provided integrated in bell-like structure 1.

As shown in FIGS. 3 a and 3 b, decontamination units 9 have a slightly rounded surface in the region of the nipple in order to abut against rounded nipple 2a in a planar and substantially full-surface manner. These decontamination units 9 provided outside recess 12 have a planar surface.

Decontamination units 9, which when view in top view are disposed radially outermost on bell-like structure 1, are arranged at the boundary between the areola and the normal breast skin.

Figure 3B:
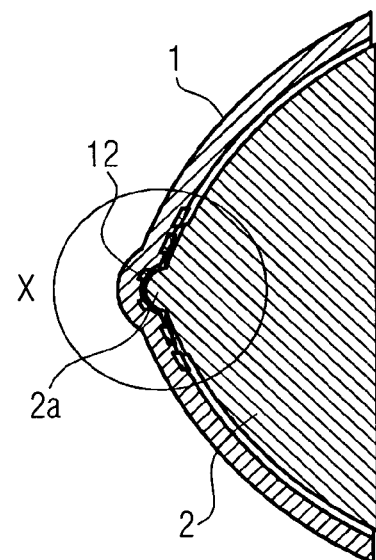
FIGS. 3b and 3c show a cross-sectional view of the embodiment from FIG. 3a, FIGS. 4a and 4b show a pad or cushion in its cross-sectional view inserted into a brassiere, where
Figure 3C:
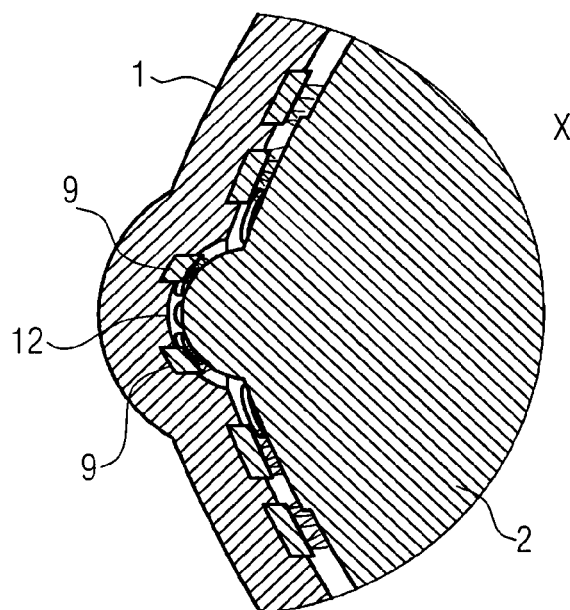

Decontamination units of FIGS. 3a to 3c can be planar light sources or else piezoceramic elements which radiate ultrasonic waves.

Although a bell-like structure 1 is provided in the present case for the embodiment of FIG. 3, a similar arrangement can also be provided within a separate pad which is inserted into a brassiere, e.g., into a pocket of a brassiere.

Figure 4A:
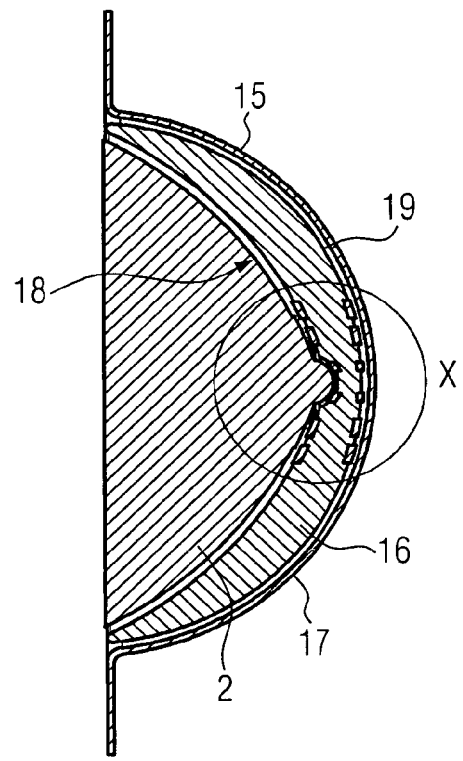
FIG. 4b shows the circled region in FIG. 4a enlarged.
Figure 4B:
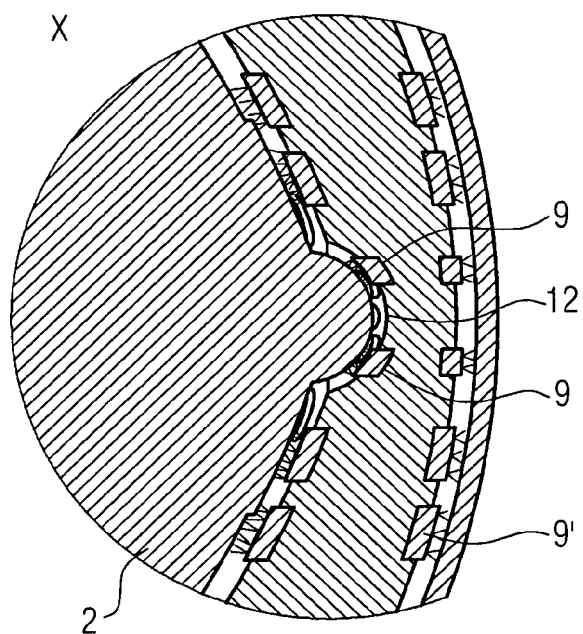

Such a pad 16 inserted into a brassiere 15 is shown in FIGS. 4a and 4b. FIG. 4b is there detail X from FIG. 4a. Pad 16 is inserted into a cup 17 of brassiere 15 Such a pad 16 can be made of cushion-like material that deforms in a sponge-like manner. In an initial state not inserted into brassiere 15, pad 16 can be shaped like a flat cushion-like structure (e.g., having two corresponding surface curvatures on opposite sides) which has no bell-like structure. Only when inserted into brassiere 15 and donned onto the breast does bell-like structure 1 shape instantaneously. When removed from the brassiere, the pad returns to its initial state. On its side 18 facing breast 2, the pad is configured like bell-like structure 1 in FIGS. 3a to c. For this reason, the individual elements shall not be described again. Same elements are denoted with the same reference numerals. In addition, however, decontamination units 9' are also provided on side 19 of pad 16 facing away from the breast.

Decontamination units 9 as well have a slightly rounded surface on side 19 of pad 16 facing away from the breast for abutting in a planar manner against the inside of cup 17. Decontamination units 9 on side 19 of pad 16 facing away from the breast are advantageous for also decontaminating cup 17 of brassiere 15.

Bell-like structure 1 in the embodiment in FIGS. 3a to 3c can be made of silicone or of plastic material or of foam material.

Figure 5:
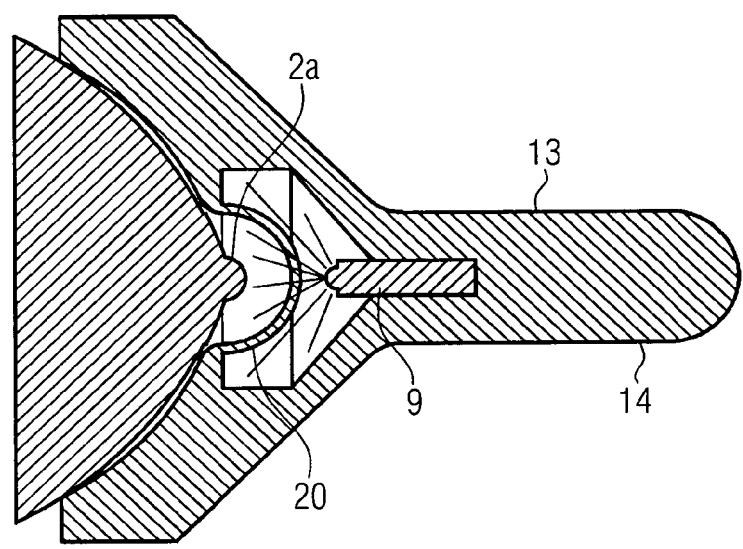
FIG. 5 shows a special apparatus which is used only for decontamination of the breast.
Figure 6:
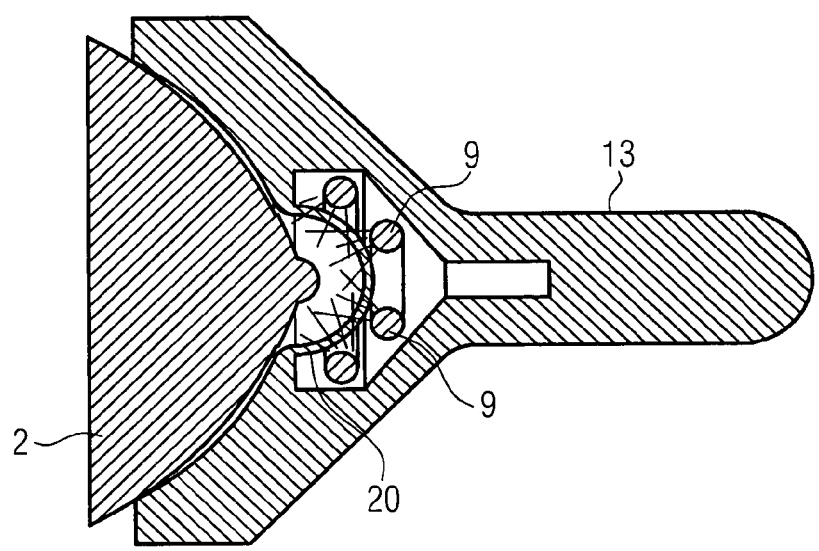
FIG. 6 shows a further example of an alternative apparatus which is used only for decontamination of the breast.

FIGS. 5 and 6 show two embodiments where the apparatus for decontamination in this case is an apparatus having only the functionality of decontamination. This means that this apparatus does not simultaneously have the function of a brassiere or the function of a breast pump, respectively.

The apparatus is configured as a kind of stamp 13 with a handle member 14 provided on the rear side. Stamp 13 has a bell-like inner surface which is slipped onto the breast. As can be seen in FIG. 5, a UV light element as a decontamination element 9 in this embodiment is also positioned opposite to nipple 2a.

The embodiment of FIG. 6 differs from the embodiment of FIG. 5 in that a plurality of decontamination elements 9 is provided treating the nipple from different sides, instead of this single decontamination element 9 which is formed opposite the nipple.

A separation wall 20 is provided in both embodiments and separates decontamination unit 9 from a space 21 formed between separation wall 20 and nipple 2a. The inner surface of stamp 13 is then easier to clean, and decontamination unit 9 does is not direct exposed to the breast. When decontamination unit 9 is a UV lamp, separation wall 20 should be UV-transparent.

FIGS. 7a to 7d show a fourth embodiment in which decontamination unit 9 is placed as a collar on the outside around bell-like structure 1 and adjoining conical taper 3.

Same features as in the embodiment of FIGS. 1 and 2 are provided with the same reference numerals and shall not be further described below. In this embodiment as well, a collection container 6 and a conduit 5 are therefore provided, via which the expressed milk is supplied to collection container 6. A vacuum generating station with reference numeral 11 is a provided here as well, via which a vacuum for expressing milk is generated.

Bell-like structure 1c and adjoining conical taper 3 are formed integrally and from uniform material. These elements can also be configured as several parts. In the present case, the entire cap, which is placed, in particular screwed onto the collection container is formed as an integral element. It can also be that only bell-like structure 1 and adjoining conical taper 3 are formed as an integral element and placed on a base member 27. Base member 27 is then placed, in particular screwed onto the collection container.

Bell-like structure 1 can be formed substantially by a front widened portion 23 facing the breast and formed like a funnel. A cylindrical tube 24 extends from the side of the widened portion facing away from the breast toward the back. This tube 24 is also referred to as a conical taper 3 and comprises e.g., a diameter that is less than opening 25 of widened portion 25 that is slipped over the breast.

In the present case, decontamination unit 9 comprises a housing 26 which is configured as a kind of collar. This collar can abut against an outer wall of widened portion 23 and against an outer wall of cylindrical tube 24 and thus can be provided at a transitional region between said portions.

Figure 7A:
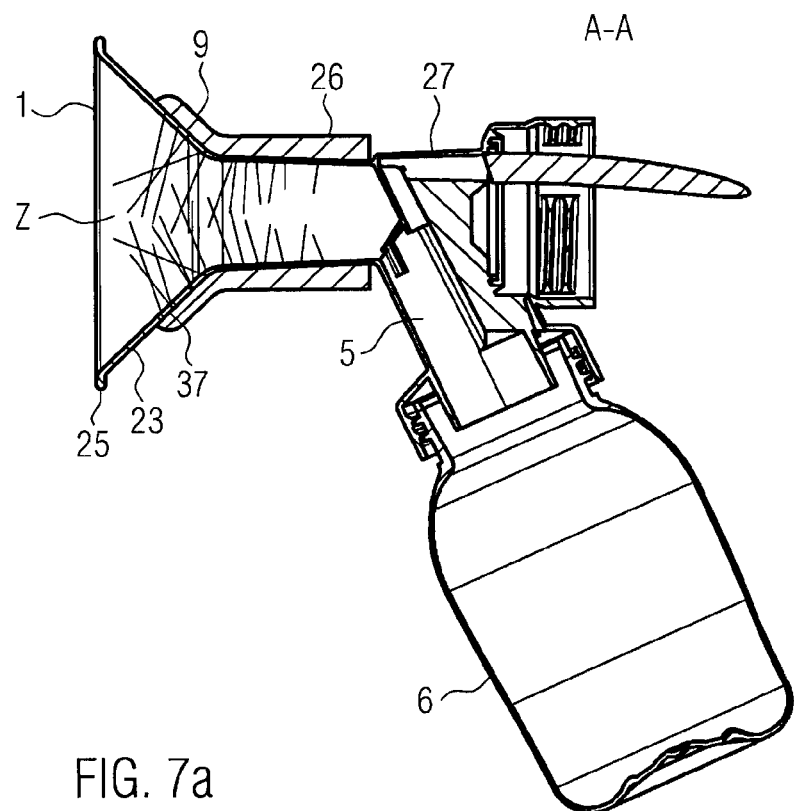
FIG. 7a shows a fourth embodiment, in which the decontamination unit is placed as a collar on the outside around the bell-like structure and the adjoining conical taper.
Figure 7B:
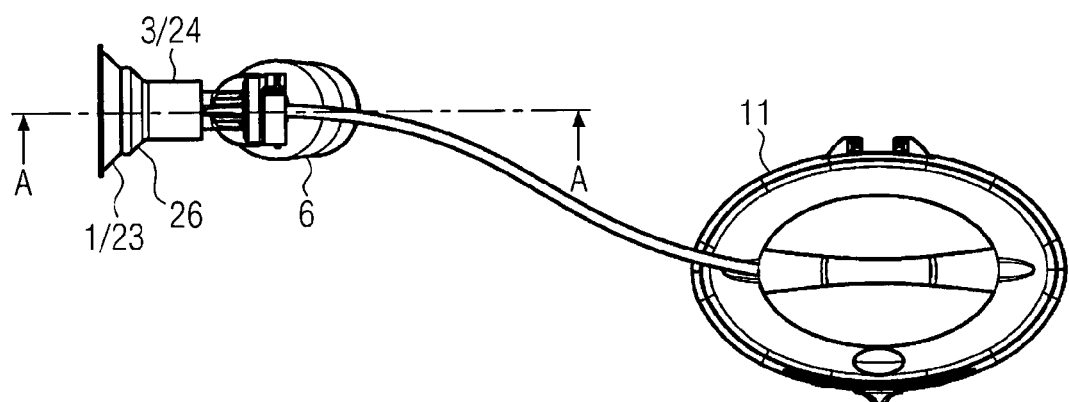
FIG. 7b shows a cross-sectional view of the embodiment from FIG. 7a along the line A-A.

Provided in the housing is a plurality of individual excitation radiation sources 37, the emitted radiation of which is illustrated by the lines indicated in FIG. 7b. The lines, each starting from a common base region, indicate the direction of the radiation.

Arranged in a region of the housing which abuts against the outer wall of widened portion 23 are excitation radiation sources 37 such that they radiate obliquely toward the breast, i.e., are aligned obliquely to a central axis Z of bell-like structure 1. In the region of cylindrical tube 24, excitation radiation sources 37 are oriented in such a manner that they are aligned perpendicular to central axis Z of the bell-like structure.

The housing accordingly has a section which can be mounted on cylindrical tube 24 (see FIG. 7b, right-hand side) and a section which can be mounted on widened portion 23 (see FIG. 7b, left-hand side). Housing 26 of the decontamination unit is therefore also on a side facing the breast formed in the manner of a funnel and has a cylindrical tube extending therefrom.

An inner wall of housing 26 presently rests substantially flat against the outer wall of widened portion 23 and against the outer wall of cylindrical tube 24 and illuminates the material from which these sections are constructed. It is then advantageous that widened portion 23 and cylindrical tube 24 are formed from material which is transparent to the excitation radiation.

When, for example, UV-C radiation is used, UV-C a radiation-transmissive material should be used.

Housing 26 of the decontamination unit can be formed as a kind of collar open on one side in its longitudinal direction, which is easily attached in a detachable manner to widened portion 23 and/or cylindrical tube 24 by way of a snap connection.

Any other attachment option is also possible. It is also possible to form a completely closed collar which is e.g., is threaded from behind onto cylindrical tube 24. For this purpose, it is advantageous to slip on cylindrical tube 24, with or without a widened portion 23 integrally formed thereon, as a separate element onto base member 27. After this housing completely closed in the circumferential direction has then been slipped on, this ensemble can then again be attached to base member 27.

Figure 7D:
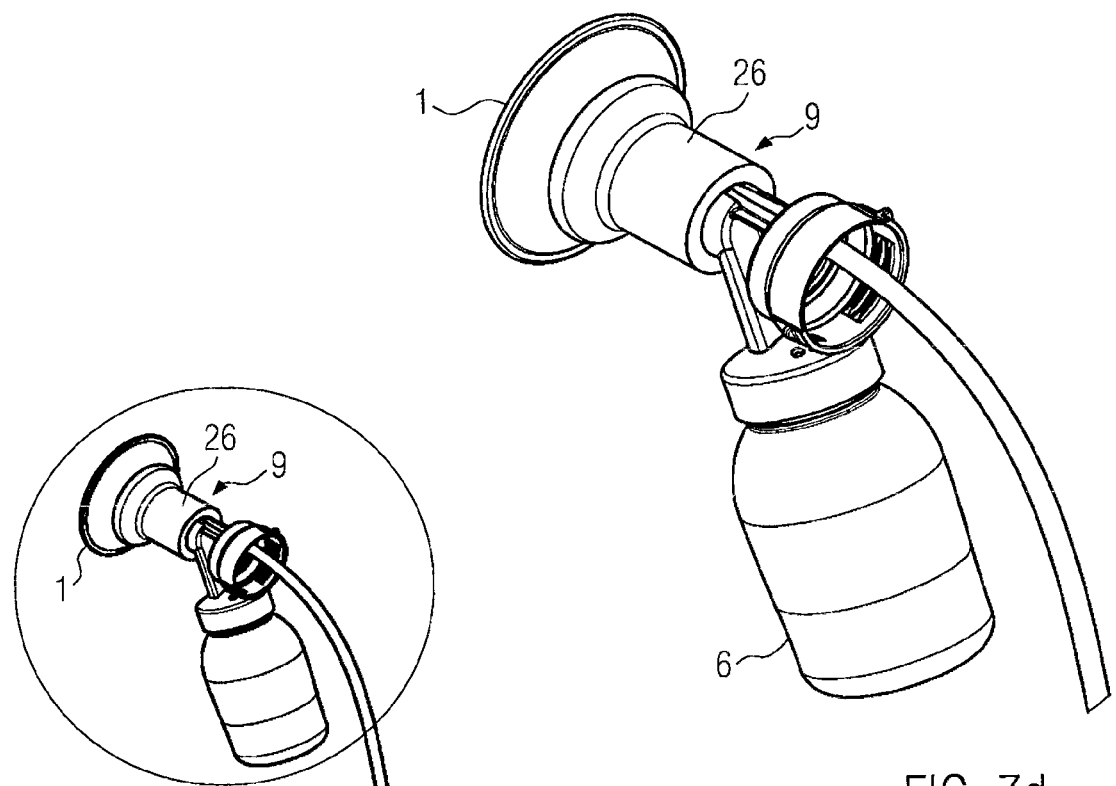
FIGS. 7c and 7d show a top view onto the embodiment of FIG. 7a obliquely from above, where
Figure 7C:
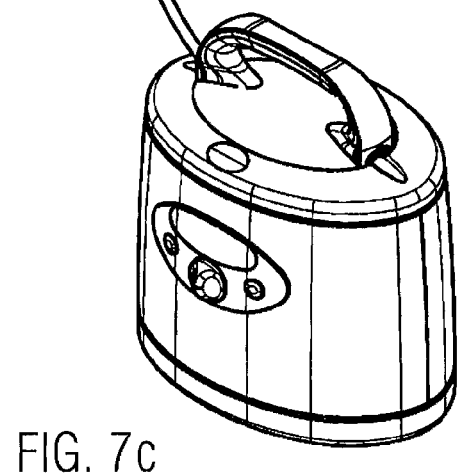

FIGS. 7c and 7d show three-dimensional views of the embodiment of FIGS. 7a and 7b, where the collar-like configuration of housing 26 of the decontamination unit can be seen.

The electronics for operating the decontamination unit can be provided in housing 26, or be connectable to a control device or energy supply device via lines that project from housing 26.

The ensemble of cylindrical tube 24 with a widened portion 23 integrally formed thereon comprises no electronic components in the present embodiment. Advantageously, base member 27 and collection container 6 comprise no electronic components, i.e., the only electronic components which can be provided with the decontamination unit removed are those of vacuum generating station 11.

Therefore, the ensemble of cylindrical tube 24 and/or widened portion 23 and/or base portion 27 and/or collection container 6 can be cleaned together or separately and preferably with liquid or steam, without problems with the electronics arising.

FIGS. 8a to d show a fifth embodiment in which decontamination unit 9 is inserted in the interior of conical taper 3.

In contrast to the embodiment from FIGS. 7a to d, the housing of decontamination unit 9 in the fifth embodiment is not provided radially on the outside of the ensemble of cylindrical tube 24 and widened portion 23, but the housing 26 is inserted into cylindrical tube 24.

Housing 26 comprises excitation radiation sources 37 at a front portion facing the breast. Excitation radiation sources 37 are disposed along a rounded wall portion which closes the housing toward the breast in a trumpet-like configuration so that they radiate onto the breast at an angle oblique to the center axis of the bell-like structure.

Figure 8A:
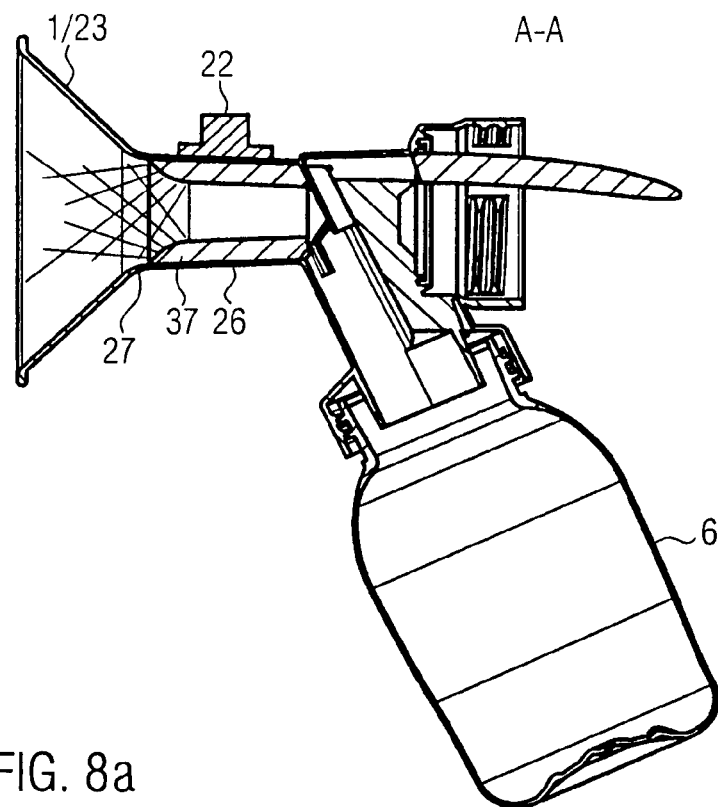
FIG. 8a shows a fifth embodiment, in which the decontamination unit is inserted into the interior of the conical taper.
Figure 8B:
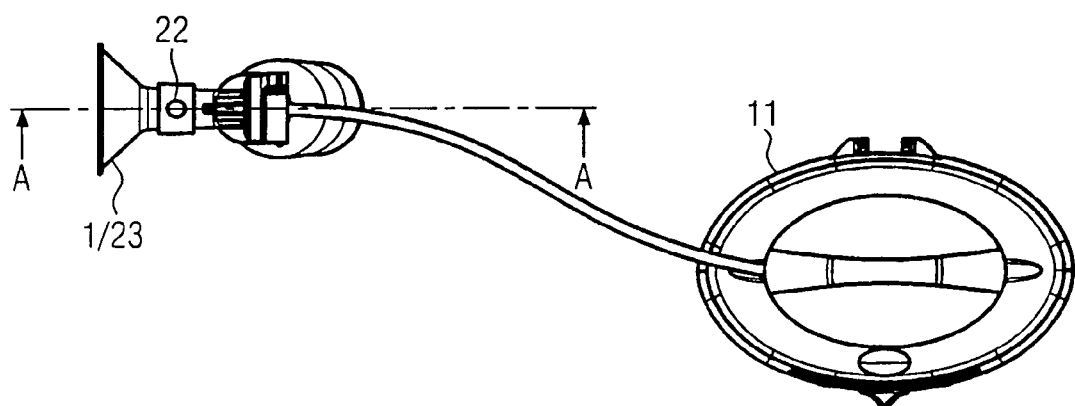
FIG. 8b shows a cross-sectional view of the embodiment from FIG. 8a along the line A-A.
Figure 8D:
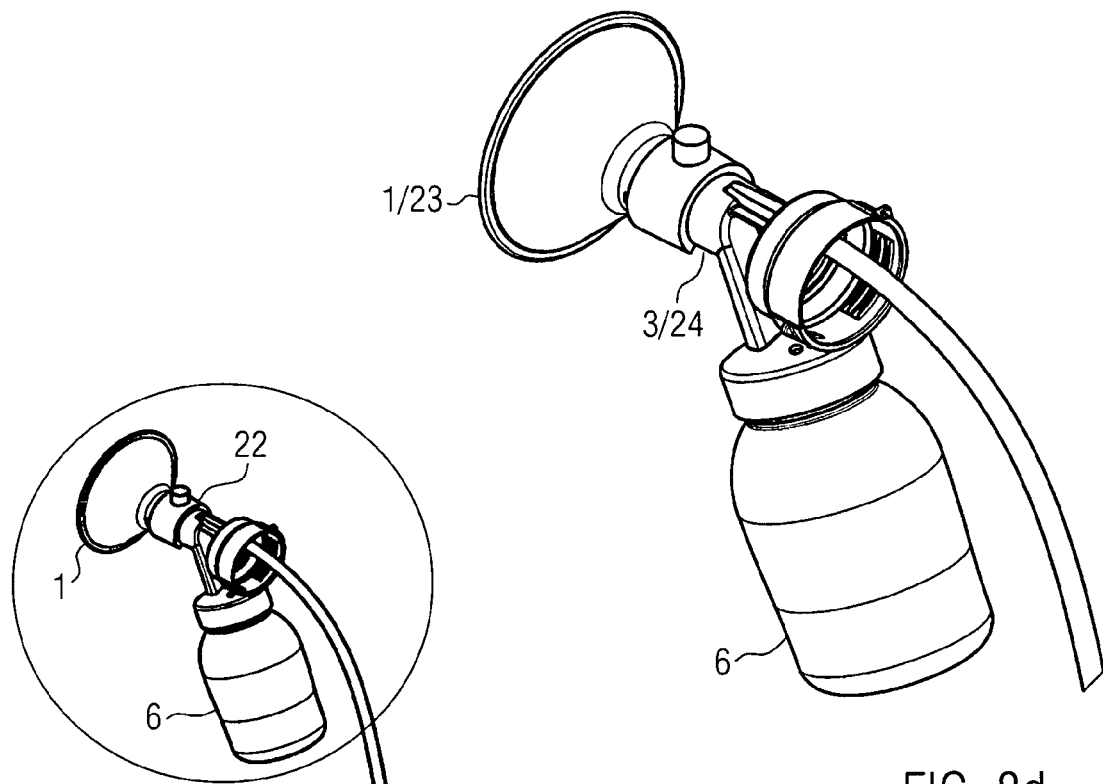
FIGS. 8c and 8d show a top view onto the embodiment of FIG. 8a obliquely from above, where
Figure 8C:
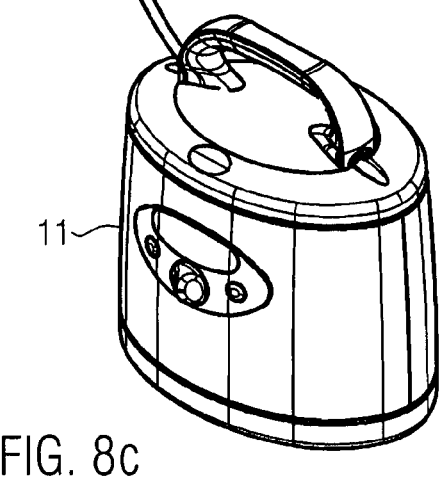

Exciter radiation sources 27 provided farthest to the right in FIG. 8a are aligned more perpendicular to center axis Z that the radiation sources provided farther to the left in FIG. 8a, where the radiation sources provided farther to the left in the housing are disposed to be more oblique.

If such an insert is used for decontamination unit 9, it is favorable to provide the power supply by way of an induction element 22 and not to use wiring, which must then, for example, pass through bell-like structure 1, but it is advantageous to provide an induction element 22. In the present case, induction element 22 is provided on the outer wall of cylindrical tube 24.

This induction element 22 can be fixedly and captively provided on cylindrical tube 24 and/or on widened portion 23, or else as a kind of collar (see FIGS. 8c and d), the cross-section of which is formed to be e.g., C-shaped, and be plugged onto widened portion 23 or cylindrical tube 24, respectively. A simple modular configuration can then be provided where the voltage or power supply of the excitation radiation sources provided in housing 26 is arranged physically separated by the wall of widened portion 23 or cylindrical tube 24, respectively.

The ensemble of cylindrical tube 24 and a widened portion 23 integrally formed thereon also in the present embodiment comprises no electronic components. Advantageously, base member 27 and collection container 6 also comprise no electronic components, i.e. the only electronic components which can be provided when the decontamination unit is removed are those of vacuum generating station 11. Therefore, the ensemble of cylindrical tube 24 and/or widened portion 23 and/or base portion 27 and/or collection container 6 can be cleaned together or separately without problems with the electronics arising.

Figure 9A:
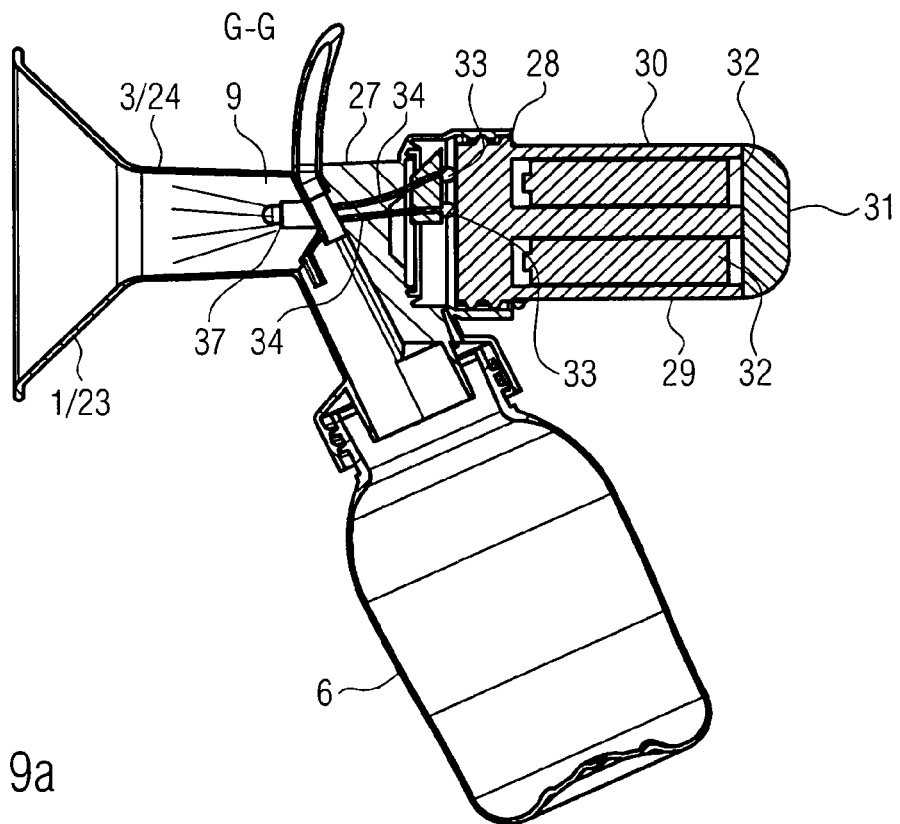
FIG. 9a shows a sixth embodiment, in which a battery pack is provided in a repeatedly detachable manner on the rear side of the decontamination apparatus.
Figure 9B:
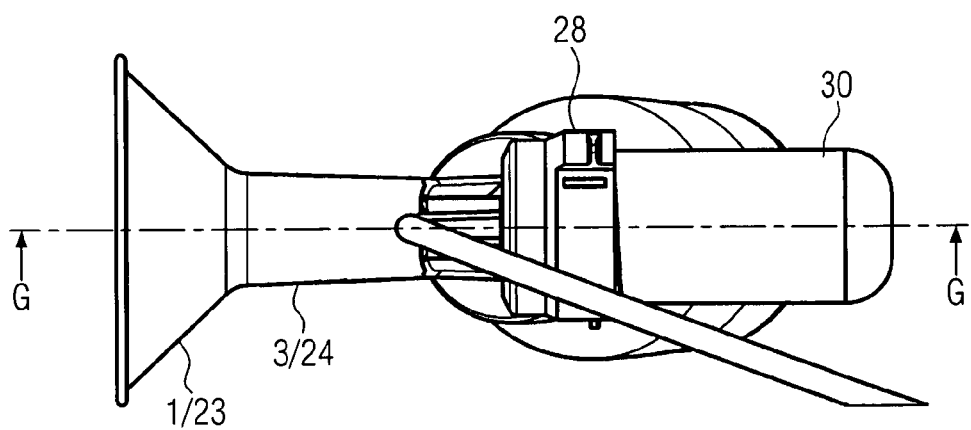
FIG. 9b shows a cross-sectional view of the embodiment from FIG. 9a along the line G-G.

FIGS. 9a and 9b show a sixth embodiment in which a battery pack is provided in a repeatedly detachable manner on the rear side of the decontamination apparatus.

In this embodiment, a mechanism for detachably connecting to a power supply 28 is provided on the rear side on base member 27. Power supply 28 is presently ensured by a battery pack 29. This battery pack 29 comprises a housing 30 and a cap 31. Provided in housing 30 of battery pack 29 are recesses into which batteries 32 are insertable. Once batteries 32 have been inserted into the recess, housing 30 is closed with cap 31 so that battery pack 29 is formed as an integral element.

Contacts, not shown in FIG. 9a, are formed on the front side of the battery pack and can be contacted with contact elements 33 which are provided on the rear side of base member 27.

Excitation radiation source 37 (a single one in the present embodiment) is connected to the battery pack 29 via lines 34 which are schematically shown in FIG. 9a and run through base member 27. Several excitation radiation sources 37 and not just a single excitation radiation source 37 can also be provided in decontamination unit 9, like in the examples of FIGS. 7 and 8.

Excitation radiation source 37 constituting decontamination unit 9 is presently provided integrally formed on base member 27. Base member 27 can be installed as a separate element between the ensemble of cylindrical tube 24 and widened portion 23, and collection container 6.

Battery pack 29 can then be connected to this base member 27 in a detachable and repeatedly connectable manner A screw connection between battery pack 29 and base member 27 is presently provided and serves as a device for the detachable connection to power supply 28.

In the embodiment of FIGS. 9a, b, the decontamination unit, in particular excitation radiation source 37, is provided in a central axis of bell-like structure 1 and on a rear wall which is formed by a wall of base member 27.

Figure 10A:
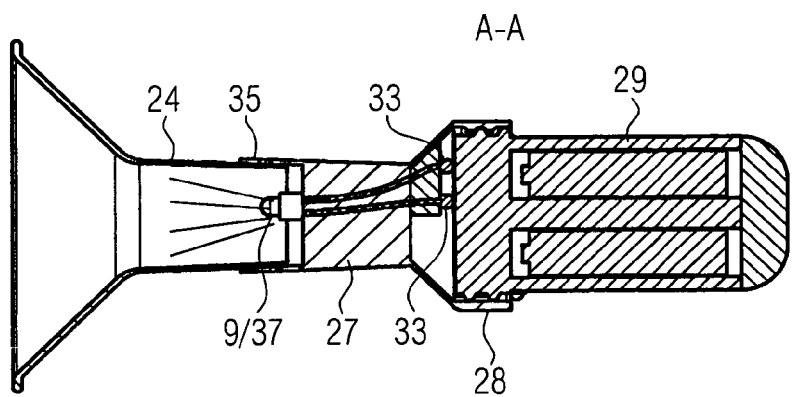
FIG. 10a shows a sixth embodiment, in which the bell-like structure is placed onto the front side of the decontamination unit.
Figure 10B:
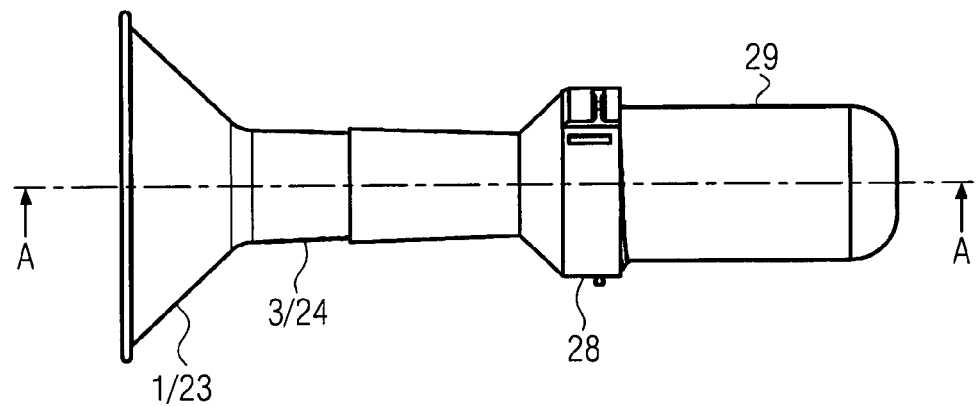
FIG. 10b shows a cross-sectional view of the embodiment from FIG. 9a along the line A-A.

FIGS. 10a and 10b show a further embodiment of the apparatus according to the invention.

In this case as well, decontamination unit, i.e., presently a single in excitation radiation source 37, is provided integrally formed in base member 27. On the rear side, i.e., on a side facing away from the breast (cf. FIG. 10a right-hand side) base member 27 has the same configuration as the base member in FIG. 9a. Consequently, contact elements 33, via which a battery pack 29 can be contacted, are there also provided.

On its side facing the breast, base member 27 comprises a cylindrical edge portion 35 which is widened in diameter as compared to cylindrical tube 24 so that a plug connection between cylindrical tube 24 and base member 27 is ensured. In the present case as well, cylindrical tube 24 is formed integrally with widened portion 23.

The entire ensemble of separate base member 27 and cylindrical tube 24 with widened portion 23 provided integrally thereon forms a kind of breast shield unit. The front portion formed by tube 24 with the widened portion 23 integrally provided thereon is separable from the rear part of the breast shield formed by base member 27. This breast shield can be coupled to battery pack 29 or a housing part of the apparatus.

The decontamination unit or the excitation radiation source, respectively, is presently provided substantially in the central axis of the bell-like structure.

Even if only a single excitation radiation source is provided in the embodiments of FIGS. 9a and b or 10a and 10b, respectively, several excitation radiation sources can also be provided there, like in the embodiments of FIGS. 8 and 7.

In the embodiments in FIGS. 7 and 8, on the other hand, the excitation radiation sources are not provided on a rear portion and in a central axis of the bell-like structure, but are arranged on an outer wall around the bell-like structure.

Figure 11A:
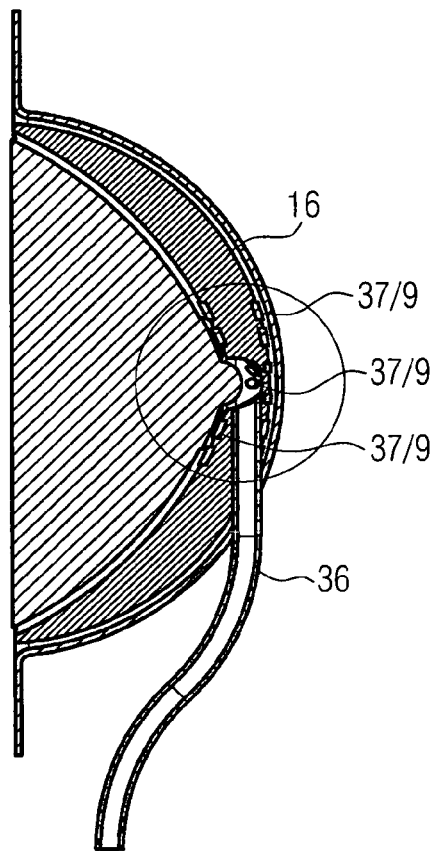
FIGS. 11a and 11b show a seventh embodiment, in which the decontamination unit is formed as a cushion or pad, respectively, where a tube barb for connecting to a pump is further provided in the pad and where
Figure 11B:
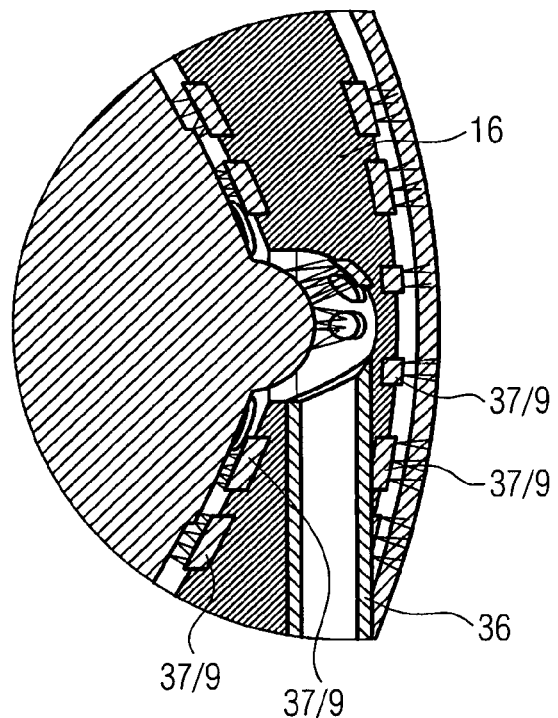

The embodiment in FIGS. 11a and 11b represents a further development of the embodiment in FIGS. 4a and 4b. For the further details, reference shall therefore presently be made to the description relating to FIGS. 4a and 4b.

Instead of the pad-like or cushion-like structure, bell-like structure 1 can also be made of a dimensionally stable, e.g. hard material which is, in particular, configured such that it does not or only slightly collapse upon the application of a vacuum. For a vacuum to be applied, it is favorable that the bell-like structure is vacuum-tight and can also be donned in a sealing manner onto the breast. The bell-like structure can be formed by a kind of rigid breast shield.

In addition, a tube barb 36 can be provided in the pad or the cushion, respectively, in the present embodiment in FIGS. 11b and 11a and terminate in the recess in the pad surrounding the areola. A pump can be connected via this tube barb so that a vacuum is generated in the recess and milk is then expressed from the breast. Due to the configuration, in which the tube barb is provided in the pad or the cushion, respectively, it is possible to offer a very inconspicuous pumping apparatus, where the brassiere can be kept on during the expression process and it is not at all visible that a decontamination and/or expression process is taking place.

In addition to the decontamination unit or the exciter radiation source described, a moisture sensor, with which e.g. a milk or liquid escape is detected, can also be provided in the apparatus.

The control device which controls the decontamination unit(s) or the exciter radiation source(s) can also comprise e.g. a functionality that the decontamination device or the exciter radiation source(s) is/are activated upon detection of liquid or a certain moisture threshold value.

LIST OF REFERENCE NUMERALS 1 bell-like structure
2 breast
2a nipple
3 conical tubular taper
4 side disposed opposite to the nipple
5 conduit
6 collection container
7 screw lid
8 lever
9, 9' decontamination unit
10 areola
11 vacuum generating station
11a vacuum tube
12 recess
13 stamp
14 handle member
15 brassiere
16 pad
17 cup
18 side facing the breast
19 side facing away from the breast
20 separation wall
21 space
22 induction element
24 cylindrical tube
23 widened portion
27 base member
25 opening
26 housing
37 excitation radiation source
28 device for detachably connecting to a power supply
29 battery pack
30 housing
31 cap
32 battery
33 contact element
34 line
35 cylindrical edge portion
36 tube barb

The invention claimed is:

1. Portable apparatus for decontamination of a breast comprising:
a widened portion oriented to face said breast so as to be able to be slipped over said breast;
a cylindrical tube extending from a side of said widened portion facing away from said breast; and
a decontamination unit which decontaminates said breast at least by way of a physical method;
wherein said decontamination unit comprises a housing in which one or more excitation radiation sources are provided, said housing being a separate element detachably mountable on said apparatus, said housing being securable by being snapped onto said apparatus for decontamination of said breast, at a section of said widened portion and at a section of said cylindrical tube; wherein said housing is a collar having a C-shaped cross-section open on one side along its longitudinal section to enable being snapped onto said apparatus.

2. Apparatus according to claim 1, wherein said decontamination unit comprises at least one of: a light source, an ultrasonic source, an ozonization source, or a plasma source.

3. Apparatus according to claim 2, wherein said widened portion has a contoured structure configured to be slipped over said breast and at least partially enclose said breast.

4. Apparatus according to claim 3, wherein said contoured structure is configured to abut against said breast in a contour-shaping manner, and the contoured structure forms a recess in a region of a nipple of said breast on an inner side of the contoured structure.

5. Apparatus according to claim 1, wherein electronics for operating said decontamination unit are connected only on said housing; and/or said apparatus for decontamination of said breast has no other source of excitation radiation except on said housing.

6. Apparatus according to claim 1, wherein said housing surrounds said widened portion and/or said cylindrical tube radially on an outside of said widened portion and/or said cylindrical tube.

7. Apparatus according to claim 1, wherein said widened portion and/or said cylindrical tube is formed to be transparent to excitation radiation from said decontamination unit at least in a section where an exciter radiation source of said decontamination unit is placed.

8. Apparatus according to claim 1, wherein said decontamination unit abuts against said breast after said apparatus has been mounted on said breast.

9. Apparatus according to claim 8, wherein said decontamination unit and at least one other decontamination unit are provided at different locations.

10. Apparatus according to claim 9, wherein said decontamination units are positioned such that they decontaminate a nipple and/or an areola of said breast when said apparatus has been mounted on said breast.

11. Apparatus according to claim 1, wherein said decontamination unit is connected to an autonomous power supply which is integrated in said apparatus.

12. Apparatus according to claim 1, including a control device which switches said decontamination unit on and/or off, and/or regulates an intensity of said decontamination unit.

13. Portable apparatus for decontamination of a breast comprising:
- a decontamination unit which decontaminates said breast at least by way of a physical method and ultraviolet radiation;
- wherein said decontamination unit is provided in a pad or a cushion made of a material which is deformable, which can be inserted as a separate element into a brassiere, wherein the pad or cushion is configured such that it is formed in an initial state in which it is not inserted into the brassiere as a flat structure, when the pad or cushion is inserted into the brassiere it is formed into a contoured structure, and wherein said pad or said cushion is provided with a tube barb via which a pump can be connected for expressing milk from said breast.

14. Apparatus according to claim 13, wherein said decontamination unit is arranged on a side of said apparatus facing said breast and a second decontamination unit is arranged on a side facing away from said breast.

15. Apparatus according to claim 13, including a control device which switches said decontamination unit on and/or off, and/or regulates an intensity of said decontamination unit.

16. A method of operating the portable apparatus of claim 1, including switching said decontamination unit on to kill microorganisms in order to prevent them from entering mammary ducts of said breast.

17. Portable apparatus for decontamination of a breast, comprising:
- a widened portion oriented to face said breast so as to be able to be slipped over said breast;
- a cylindrical tube extending from a side of said widened portion facing away from said breast; and
- a decontamination unit which decontaminates said breast at least by way of a physical method;
- wherein said decontamination unit comprises a housing in which one or more excitation radiation sources are provided, said housing being a separate element detachably mountable on said apparatus, said housing being inserted into said widened portion and/or at a section of said cylindrical tube, and is operable by way of an induction element placed on the outside of said widened portion and/or said cylindrical tube.

* * * * *